United States Patent
Weiguny et al.

(10) Patent No.: US 6,803,473 B2
(45) Date of Patent: Oct. 12, 2004

(54) METHOD FOR PRODUCING MALEIC ACID ANHYDRIDE

(75) Inventors: Jens Weiguny, Freinsheim (DE); Sebastian Storck, Mannheim (DE); Andreas Tenten, Maikammer (DE); Wilhelm Ruppel, Mannheim (DE)

(73) Assignee: BASF Aktiengesellschaft, Ludwigshafen (*) Notice: Subject to any disclaimer, the term of this patent is extended or adjusted under 35 U.S.C. 154(b) by 83 days.

(21) Appl. No.: 10/220,746

(22) PCT Filed: Mar. 6, 2001

(86) PCT No.: PCT/EP01/02496

§ 371 (c)(1),
(2), (4) Date: Sep. 5, 2002

(87) PCT Pub. No.: WO01/68626

PCT Pub. Date: Sep. 20, 2001

(65) Prior Publication Data

US 2003/0065194 A1 Apr. 3, 2003

(30) Foreign Application Priority Data

Mar. 10, 2000 (DE) .......................................... 100 11 309

(51) Int. Cl.⁷ ............................................ C07D 307/60
(52) U.S. Cl. ...................................................... 549/259
(58) Field of Search ................................. 549/259, 260

(56) References Cited

U.S. PATENT DOCUMENTS

| | | |
|---|---|---|
| 3,147,084 A | 9/1964 | Franzen |
| 3,296,282 A | 1/1967 | Kerr |
| 3,871,445 A | 3/1975 | Wanka |
| 4,203,906 A | 5/1980 | Takada |
| 4,231,943 A | 11/1980 | Paradis |
| 4,429,137 A | 1/1984 | Blum |
| 4,515,899 A | 5/1985 | Click |
| 4,562,268 A | 12/1985 | Wrobleski |
| 4,795,818 A | 1/1989 | Becker |
| 4,933,312 A | 6/1990 | Haddad |
| 5,011,945 A | 4/1991 | Taheri |
| 5,021,588 A | 6/1991 | Contractor |
| 5,095,125 A | 3/1992 | Haddad |
| 5,137,860 A | 8/1992 | Ebner |
| 5,158,923 A | 10/1992 | Barone |
| 5,168,090 A | 12/1992 | Ebner |
| 5,185,455 A | 2/1993 | Ebner |
| 5,225,574 A | 7/1993 | Aichinger |
| 5,275,996 A | 1/1994 | Andrews |
| 5,296,436 A | 3/1994 | Bortinger |
| 5,641,722 A | 6/1997 | Mitchell |
| 5,739,391 A | 4/1998 | Ruppel |
| 5,773,382 A | 6/1998 | Mitchell |
| 5,821,390 A | 10/1998 | Ruppel |

FOREIGN PATENT DOCUMENTS

| | | |
|---|---|---|
| DE | 2 201 528 | 11/1972 |
| DE | 25 13 405 | 10/1976 |
| DE | 28 30 765 | 1/1980 |
| DE | 29 03 582 | 11/1980 |
| EP | 056 901 | 8/1982 |
| EP | 099 431 | 2/1984 |
| EP | 123 467 | 10/1984 |
| EP | 383 224 | 8/1990 |
| EP | 435 951 | 10/1991 |
| EP | 700 714 | 3/1996 |
| EP | 700 893 | 3/1996 |
| WO | 93/01155 | 1/1993 |
| WO | 97/26817 | 10/1995 |
| WO | 97/12674 | 4/1997 |
| WO | 97/43242 | 11/1997 |

OTHER PUBLICATIONS

Chem.Eng.Sci.,vol. 41,No. 4, 765–772,1986,Wellauer et al.
Ull.Enc.Ind.Chem.6th Ed.,Oxidation of Benzen, 1999.

*Primary Examiner*—Bernard Dentz
(74) *Attorney, Agent, or Firm*—Keil & Weinkauf (57) ABSTRACT

In a process for preparing maleic anhydride by heterogeneously catalyzed gas-phase oxidation of hydrocarbons having at least four carbon atoms using oxygen-containing gases in the presence of a volatile phosphorus compound over a catalyst comprising vanadium, phosphorus and oxygen in a shell-and-tube reactor unit having at least two successive cooled reaction zones, the temperature of the first reaction zone is from 350 to 450° C. and the temperature of the second and further reaction zones is from 350 to 480° C. and the temperature difference between the hottest reaction zone and the coolest reaction zone is at least 2° C.

7 Claims, 3 Drawing Sheets

Fig. 1

Figure 3:
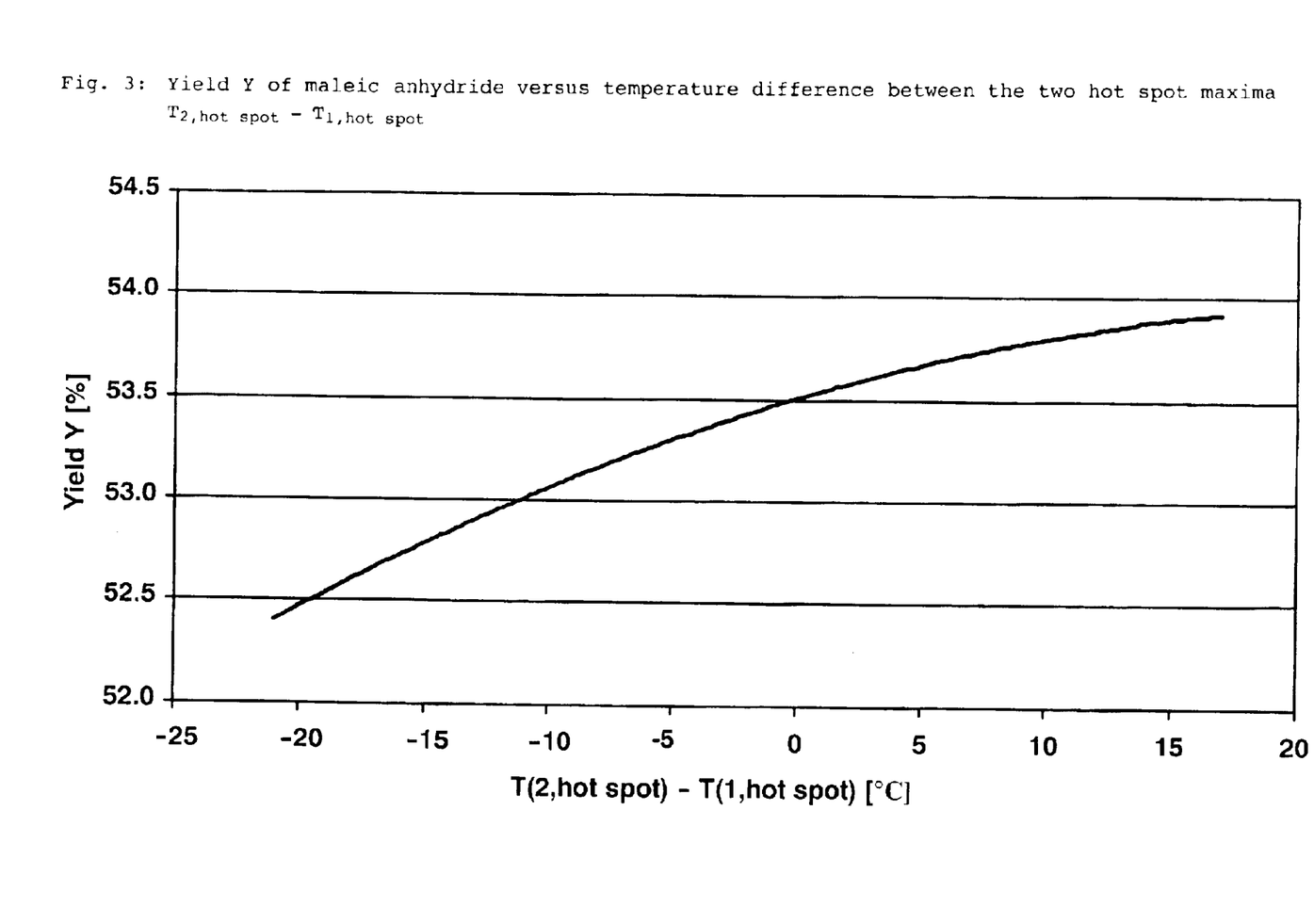

Fig. 3: Yield Y of maleic anhydride versus temperature difference between the two hot spot maxima $T_{2,\text{hot spot}} - T_{1,\text{hot spot}}$

METHOD FOR PRODUCING MALEIC ACID ANHYDRIDE

This application is a 371 of PCT/EP01/02496 filed Mar. 6, 2001.

The present invention relates to a process for preparing maleic anhydride by heterogeneously catalyzed gas-phase oxidation of hydrocarbons having at least four carbon atoms using oxygen-containing gases in the presence of a volatile phosphorus compound over a catalyst comprising vanadium, phosphorus and oxygen in a shell-and-tube reactor unit having at least two successive cooled reaction zones.

Maleic anhydride is an important intermediate in the synthesis of γ-butyrolactone, tetrahydrofuran and 1,4-butanediol, which are in turn used as solvents or are processed further to give, for example, polymers such as polytetrahydrofuran or polyvinylpyrrolidone.

The preparation of maleic anhydride by heterogeneously catalyzed gas-phase oxidation of hydrocarbons having at least four carbon atoms using oxygen in a shell-and-tube reactor over a catalyst comprising vanadium, phosphorus and oxygen is generally known and described, for example, in Ullmann's Encyclopedia of Industrial Chemistry, $6^{th}$ edition, 1999 Electronic Release, Chapter "MALEIC AND FUMARIC ACID—Maleic Anhydride". In general, benzene or $C_4$-hydrocarbons such as 1,3-butadiene, n-butenes or n-butane are reacted. The catalysts comprising vanadium, phosphorus and oxygen, hereinafter referred to as "VPO catalysts", are used in unpromoted (see U.S. Pat. Nos. 4,429,137, 4,562,268, 5,641,722 and 5,773,382) or promoted (see U.S. Pat. No. 5,011,945, 5,158,923 and 5,296,436) form. According to U.S. Pat. No. 4,562,268, Example 18, a maximum space-time yield of 76 g/lh, i.e. 76 g of maleic anhydride per 1 of catalyst and hour, is achieved. For the purposes of the present invention, the space-time yield is the amount of desired product, i.e. maleic anhydride, in grams produced per hour and volume of the catalyst bed in liters in continuous operation.

The most important objective of the heterogeneously catalyzed gas-phase oxidations of hydrocarbons to maleic anhydride is essentially to achieve a very high space-time yield over a long period of some months.

Thus, it was recognized in U.S. Pat. No. 3,296,282 that deactivation of the VPO catalyst can be suppressed by addition of an organic phosphorus compound. The best results were achieved when the phosphorus compound was fed in after interruption of the oxidation reaction. In the oxidation of 2-butene, a maximum space-time yield of 77 g/lh was able to be achieved (see Example 1 in the document cited).

EP-A-0 123 467 teaches that the addition of the phosphorus compound can also be carried out continuously during the oxidation reaction with addition of steam. In the oxidation of n-butane, a space-time yield of 68 g/lh was achieved (see Example 1 in the document cited).

In U.S. Pat. No. 4,515,899, it was recognized that the activity of the VPO catalyst is damped by addition of a phosphorus compound. This makes possible a higher hydrocarbon throughput at improved selectivity, which leads to an increased space-time yield. In the oxidation of n-butane, a space-time yield of 90 g/lh was achieved (see Example 3 in the document cited).

U.S. Pat. NO. 5,185,455 discloses optimization of the process parameters in the oxidation of n-butane to maleic anhydride-over a VPO catalyst in the continual presence of trimethyl phosphate and water vapor. The maximum space-time yield achieved was 104 g/lh (see Example 2 in the document cited).

The conversion of the hydrocarbons into maleic anhydride is strongly exothermic and is accompanied by many possible parallel and subsequent reactions. Consequently, an increase in the hydrocarbon throughput, which is desirable for achieving a high space-time yield, results in a decrease in the selectivity of desired product formation at the same hydrocarbon conversion due to the increased generation of heat.

EP-A-0 099 431 has proposed countering the abovementioned effect of reduced selectivity at increased generation of heat by use of a structured catalyst bed, i.e. a bed in which the activity varies according to position. The lowest catalyst activity is at the reactor inlet and the highest is at the reactor outlet. In between, it can vary continuously or in steps. For the targeted setting of the catalyst activities, the document teaches essentially dilution of the active catalyst particles with inert material and the use of catalysts of differing activity and possibly mixtures thereof.

U.S. Pat. No. 5,011,945 describes the use of a structured catalyst bed in the oxidation of n-butane over a VPO catalyst in the presence of a volatile phosphorus compound, with the unreacted n-butane being recirculated after maleic anhydride and by-products have been separated off. The lowest catalyst activity is at the reactor inlet and the highest is at the reactor outlet. A space-time yield of at most 95 g/lh is described.

WO 93/01155 discloses a process for preparing maleic anhydride from n-butane over a VPO catalyst in the presence of a volatile phosphorus compound, in which the catalyst activity is varied with temperature and n-butane concentration in the flow direction of the gas in such a way that the reaction rate is promoted by high activity in a region of low temperature and low n-butane concentration within the bed and is damped by low activity in a critical region within the bed where the combination of temperature and n-butane concentration would lead to an excessive increase in conversion and reaction temperature. The maximum space-time yield achieved was 129 g/lh (see Example 6 in the document cited).

Wellauer et al., Chem. Eng. Sci. Vol. 41, No. 4 (1986), pages 765 to 772, describe a simulation model for the oxidation of n-butane to maleic anhydride on the basis of experimental data for a known catalyst. With the objective of a simple modeling concept, the hot spot maximum, i.e. the maximum temperature in the catalyst bed resulting from the exothermic reaction, was identified as critical parameter in terms of yield. The publication teaches two measures for optimizing the process: (a) the use of two catalyst beds with a low activity at the reactor inlet and a high activity at the reactor outlet and (b) the setting of two different salt bath temperatures. Even by mathematical optimization, it was only possible to achieve an increase in the experimentally determined space-time yield from 60 g/lh to 62 g/lh for (a) and 63 g/lh for (b) compared to the comparative method using a catalyst bed at a constant salt bath temperature (see Table 2 in the document cited).

According to the present invention, it was recognized that the n-butane throughput over the catalyst can no longer be increased significantly under the conditions disclosed in Wellauer et al., since the temperature of the hot spot maxima would increase significantly. This in turn would result in a significant reduction in the selectivity and thus a significant decrease in the yield and space-time yield.

It is an object of the present invention to develop a process for preparing maleic anhydride by heterogeneously catalyzed gas-phase oxidation of a hydrocarbon having at least four carbon atoms using oxygen, which makes it possible to achieve, at high hydrocarbon throughput over the catalyst, a high conversion, a high selectivity and a high yield of desired product and thus a significantly higher space-time yield than according to the prior art. A further object of the present invention was to find flexible reaction conditions which make it possible to obtain a high space-time yield over a prolonged period even in the event of fluctuations in the amount, quality or purity of the starting materials or in the event of progressive catalyst deactivation.

We have found that these objects are achieved by a process for preparing maleic anhydride by heterogeneously catalyzed gas-phase oxidation of hydrocarbons having at least four carbon atoms using oxygen-containing gases in the presence of a volatile phosphorus compound over a catalyst comprising vanadium, phosphorus and oxygen in a shell-and-tube reactor unit having at least two successive cooled reaction zones, wherein the temperature of the first reaction zone is from 350 to 450° C. and the temperature of the second and further reaction zones is from 350 to 480° C. and the temperature difference between the hottest reaction zone and the coolest reaction zone is at least 2° C.

For the purposes of the present invention, the term shell-and-tube reactor unit refers to a unit comprising at least one shell-and-tube reactor. A shell-and-tube reactor in turn comprises at least one reactor tube which is surrounded by a heat transfer medium for heating and/or cooling. In general, shell-and-tube reactors used industrially contain from a few hundred to tens of thousands of reactor tubes connected in parallel. If a plurality of individual shell-and-tube reactors (in the sense of shell-and-tube reactor apparatuses) are connected in parallel, these are considered to be the equivalent of a shell-and-tube reactor and are included under the term shell-and-tube reactor as used below.

If the shell-and-tube reactor unit comprises a plurality of shell-and-tube reactors, for example two, three, four or more, these are connected in series. In general, the shell-and-tube reactors are then connected in direct sequence, i.e. the output stream from one shell-and-tube reactor is conveyed directly to the inlet of the following reactor. However, it is also possible for mass and/or energy to be removed and/or introduced between the two shell-and-tube reactors. Thus, for example, part of the gas stream or a component thereof can be taken off or a further gas stream can be introduced or the gas stream can be passed through a heat exchanger.

An essential aspect of the process of the present invention is the use of a shell-and-tube reactor unit which has at least two successive reaction zones and is operated at the abovementioned temperatures with adherence to the temperature difference specified. For the purposes of the present invention, the term reaction zone refers to a region within a shell-and-tube reactor in which a catalyst is present and the temperature is maintained at a uniform value. In this context, the temperature of a reaction zone is the temperature at which the catalyst in this reaction zone would be if the process were carried out in the absence of a chemical reaction. If this temperature is not exactly the same at all points, the term refers to the arithmetic mean of the temperatures along the reaction zone. The first, second or further reaction zones are in each case the first, second or further reaction zones in the direction in which the gas is passed through.

Depending on the embodiment, a shell-and-tube reactor can have one, two, three or even more successive reaction zones. If a shell-and-tube reactor has more than one reaction zone, use is generally made of physically separate heat transfer media.

The shell-and-tube reactor unit which can be used in the process of the present invention may, for example, be achieved
in the case of two successive reaction zones by means of
    a two-zone shell-and-tube reactor
    two single-zone shell-and-tube reactors connected in series
or in the case of three successive reaction zones by means of
    a three-zone shell-and-tube reactor
    a two-zone shell-and-tube reactor together with a single-zone shell-and-tube reactor connected in series
    a single-zone shell-and-tube reactor together with a two-zone shell-and-tube reactor connected in series
    three single-zone shell-and-tube reactors connected in series.

Furthermore, the shell-and-tube reactor unit can also have one or more preheating zones which heat the incoming gas mixture. A preheating zone integrated into a shell-and-tube reactor can be achieved, for example, by means of reactor tubes which are filled with inert material and are likewise surrounded by heat transfer medium. As inert material, it is in principle possible to use all shaped bodies which are chemically inert, i.e. induce or catalyze no heterogeneous catalytical reaction, and which result in a maximum pressure drop below the respective, maximum tolerable plant-specific value. Suitable inert materials are, for example, oxidic materials such as $Al_2O_3$ or SiC or metallic materials such as stainless steel. Examples of shaped bodies are spheres, pellets, hollow cylinders, rings, trilobes, tristars, wagon wheels, extrudates or irregular crushed bodies.

The temperature in the first reaction zone in the flow direction is from 350 to 450° C., preferably from 380 to 440° C. and particularly preferably from 380 to 430° C. The temperatures in the second and further reaction zones in the flow direction are from 350 to 480° C., preferably from 380 to 460° C. and particularly preferably from 400 to 450° C. The temperature difference between the hottest reaction zone and the coolest reaction zone is at least 2° C. In general, the hottest reaction zone is downstream of the coolest reaction in the flow direction, with further reaction zones being able to be located in between. For the embodiment having two successive reaction zones, this means that the temperature of the second reaction zone is at least 2° C. above the temperature of the first reaction zone.

In the embodiments having three successive reaction zones, there are in principle a number of possibilities according to the present invention. In the interests of simplicity, the zones are numbered from 1 to 3 in the flow direction and the temperature is abbreviated as T in the following.

a) "T(zone 2)–T(zone 1)" conforms to the minimum temperature difference according to the present invention, i.e. T(zone 2) is the highest temperature and T(zone 1) is the lowest temperature upstream of the hottest zone. Thus, T(zone 3) is by definition lower than T(zone 2).
b) "T(zone 3)–T(zone 1)" conforms to the minimum temperature difference according to the present invention, i.e. T(zone 3) is the highest temperature and T(zone 1) is the lowest temperature upstream of the hottest zone. Thus, T(zone 2) is by definition between T(zone 1) and T(zone 3).
c) "T(zone 3)–T(zone 2)" conforms to the minimum temperature difference according to the present invention, i.e. T(zone 3) is the highest temperature and T(zone 2) is the lowest temperature upstream of the hottest zone. Thus, T(zone 1) is by definition between T(zone 2) and T(zone 3).

Preference is given to case (b) in which the temperature increases from zone to zone in the flow direction. This also applies if there are more than three successive reaction zones.

The temperature difference between the hottest and coolest reaction zones is preferably at least 5° C., particularly preferably at least 8° C., very particularly preferably at least 10° C. and in particular at least 12° C.

Furthermore, it has surprisingly been found that the yield of desired product, i.e. maleic anhydride, depends significantly on the temperature difference between the hot spot maxima established. For the purposes of the present invention, a hot spot maximum is the maximum temperature measured in the catalyst bed within a reaction zone during the chemical reaction. In general, the hot spot maximum is located neither directly at the beginning nor directly at the end of a reaction zone, so that the temperature before and after the hot spot maximum is lower. If there is no maximum temperature within a catalyst bed of a reaction zone, i.e. every point is at the same temperature, then this temperature is taken as the hot spot maximum. The yield of desired product increases with increasing temperature difference between the hot spot maximum of the second or subsequent reaction zone and the hot spot maximum of a preceding reaction zone. The hot spot maximum of the first, second or subsequent reaction zone is in each case the hot spot maximum of the first, second or subsequent reaction zone in the direction in which the gas passes through.

In a preferred embodiment, at least one hot spot maximum of the second or subsequent reaction zone is higher than all hot spot maxima in preceding reaction zones. For the simple embodiment with two successive reaction zones, this means that the hot spot maximum of the second reaction zone is higher than that of the first. For the embodiment with three successive reaction zones, it means either that the hot spot maximum of the third reaction zone is higher than the hot spot maxima of the first and second zones, or that at least the hot spot maximum of the second reaction zone is higher than the hot spot maximum of the first zone.

Hydrocarbons which can be used in the process of the present invention are aliphatic and aromatic, saturated and unsaturated hydrocarbons having at least four carbon atoms, for example 1,3-butadiene, 1-butene, 2-cis-butene, 2-trans-butene, n-butane, $C_4$ mixtures, 1,3-pentadiene, 1,4-pentadiene, 1-pentene, 2-cis-pentene, 2-trans-pentene, n-pentane, cyclopentadiene, dicyclopentadiene, cyclopentene, cyclopentane, $C_5$ mixtures, hexenes, hexanes, cyclohexane and benzene. Preference is given to using 1-butene, 2-cis-butene, 2-trans-butene, n-butane, benzene or mixtures thereof. Particular preference is given to using n-butane, for example as pure n-butane or as a component of n-butane-containing gases and liquids. The n-butane used can originate, for example, from natural gas, from steam crackers or from FCC plants.

The addition of the hydrocarbon is generally quantity-regulated, i.e. with continual setting of a defined amount per unit time. The hydrocarbon can be metered in in liquid or gaseous form. Preference is given to metered addition in liquid form with subsequent vaporization before entry into the shell-and-tube reactor unit.

Oxidants used are oxygen-containing gases, for example air, synthetic air, a gas enriched with oxygen or else "pure" oxygen, i.e. oxygen obtained, for example, from fractionation of liquid air. The oxygen-containing gas is also added under quantity regulation.

The gas to be passed through the shell-and-tube reactor unit generally contains inert gas. The proportion of inert gas at the beginning is usually from 30 to 90% by volume. Inert gases are all gases which do not contribute directly to formation of maleic anhydride, for example nitrogen, noble gases, carbon monoxide, carbon dioxide, steam, oxygenated and nonoxygenated hydrocarbons having fewer than four carbon atoms, (e.g. methane, ethane, propane, methanol, formaldehyde, formic acid, ethanol, acetaldehyde, acetic acid, propanol, propionaldehyde, propionic acid, acrolein, crotonaldehyde, acrylic acid) and mixtures thereof. In general, the inert gas is introduced into the system via the oxygen-containing gas. However, it is also possible to introduce further inert gases separately. Introduction of further inert gases, which may, for example, come from the partial oxidation of the hydrocarbons, is possible via partial recirculation of the reaction product, if desired after work-up.

To ensure a long catalyst life and further increases in conversion, selectivity, yield, throughput over the catalyst and space-time yield, a volatile phosphorus compound is introduced into the gas in the process of the present invention. Its concentration at the beginning, i.e. at the reactor inlet, is at least 0.1 ppm by volume, i.e. $0.1 \times 10^{-6}$ parts by volume of volatile phosphorus compounds based on the total volume of the gas at the reactor inlet. Preference is given to a content of from 0.2 to 20 ppm by volume, particularly preferably from 0.5 to 5 ppm by volume. For the purposes of the present invention, volatile phosphorus compounds are all phosphorus-containing compounds which are gaseous in the desired concentration under the use conditions. Examples which may be mentioned are the compounds of the formulae (I) and (II)

(I)

(II)

where $X^1$, $X^2$ and $X^3$ are, independently of one another, hydrogen, halogen, $C_1$–$C_6$-alkyl, $C_3$–$C_6$-cycloalkyl, $C_6$–$C_{10}$-aryl, $C_1$–$C_6$-alkoxy, $C_3$–$C_6$-cycloalkoxy or $C_6$–$C_{10}$-aroxy. Preference is given to compounds of the formula (III)

(III)

where $R^1$, $R^2$ and $R^3$ are, independently of one another, hydrogen, $C_1$–$C_6$-alkyl, $C_3$–$C_6$-cycloalkyl or $C_6$–$C_{10}$-aryl. Particular preference is given to compounds of the formula (III) in which $R^1$, $R^2$ and $R^3$ are, independently of one another, $C_1$–$C_4$-alkyl such as methyl, ethyl, propyl, 1-methylethyl, butyl, 1-methylpropyl, 2-methylpropyl or 1,1-dimethylethyl, preferably tri($C_1$–$C_4$-alkyl) phosphate. Very particular preference is given to trimethyl phosphate, triethyl phosphate and tripropyl phosphate, in particular triethyl phosphate.

The process of the present invention can be carried out at a pressure below atmospheric pressure (e.g. down to 0.05 MPa abs) or above atmospheric pressure (e.g. up to 10 MPa abs). By this pressure is meant the pressure prevailing in the shell-and-tube reactor unit. Preference is given to a pressure of from 0.1 to 1 MPa abs, particularly preferably from 0.1 to 0.5 MPa abs.

Possible catalysts for the process of the present invention are all those whose active composition comprises vanadium, phosphorus and oxygen. Thus, for example, it is possible to use catalysts in which no promoters are present, for example as described in U.S. Pat Nos. 5,275,996, 5,641,722, 5,137,860, 5,095,125, 4,933,312 or EP-A-0 056 901.

Furthermore, it is possible to use catalysts which further comprise other components in addition to vanadium, phosphorus and oxygen. In principle, components comprising elements of groups 1 to 15 of the Periodic Table can be added. The content of additives in the finished catalyst is generally not more than about 5% by weight, in each case calculated as oxide. Examples may be found in WO 97/12674, WO 95/26817, U.S. Pat. Nos. 5,137,860, 5,296,436, 5,158,923 or 4,795,818. Preferred additives are compounds of the elements cobalt, molybdenum, iron, zinc, hafnium, zirconium, lithium, titanium, chromium, manganese, nickel, copper, boron, silicon, antimony, tin, niobium and bismuth.

Suitable catalysts can, for example, be produced as follows:

a) reacting a pentavalent vanadium compound (e.g. $V_2O_5$) with an organic reducing solvent (e.g. an alcohol such as isobutanol) in the presence of a pentavalent phosphorus compound (e.g. orthophosphoric and/or pyrophosphoric acid) with heating;
b) isolating the VPO catalyst precursor formed (e.g. by filtration or evaporation);
c) drying the VPO catalyst precursor, and possibly initial preactivation by additional elimination of water from the VPO mixture;
d) shaping (e.g. tabletting, if desired with addition of a lubricant such as graphite and, if desired, addition of a pore former such as stearic acid);
e) preactivating the VPO catalyst precursor by heating in an atmosphere comprising oxygen, nitrogen, noble gases, carbon dioxide, carbon monoxide and/or water vapor. The catalyst performance can be influenced by a suitable combination of temperatures, treatment times and gas atmospheres matched to the respective catalyst system.

If additives are used, they can in principle be added at any stage of catalyst production, either as solution, solid or gaseous component. The additives are advantageously added in step (a) of the general description of the production of the VPO catalyst precursor given above.

In general, the catalysts used in the process of the present invention have an atomic phosphorus/vanadium ratio of from 0.9 to 1.5, preferably from 0.9 to 1.2 and particularly preferably from 1.0 to 1.1. The mean oxidation state of the vanadium is generally from +3.9 to +4.4, preferably from 4.0 to 4.3. The catalysts used generally have a BET surface area of from 10 to 50 $m^2/g$, preferably from 15 to 30 $m^2/g$. They generally have a pore volume of from 0.1 to 0.5 ml/g, preferably from 0.1 to 0.3 ml/g. The bulk density of the catalysts used is generally from 0.5 to 1.5 kg/l, preferably from 0.5 to 1.0 kg/l.

The catalysts are generally used as shaped bodies having a mean size above 2 mm. Owing to the need to pay attention to the pressure drop in carrying out the process, smaller shaped bodies are generally unsuitable. Suitable shaped bodies are, for example, pellets, cylinders, hollow cylinders, rings, spheres, rods, wagon wheels or extrudates. Particular shapes such as "trilobes" and "tristars" (see EP-A-0 593 646) or shaped bodies having at least one notch on the outside (see U.S. Pat. No. 5,168,090) are likewise possible.

In general, use is made of unsupported catalysts, i.e. the entire shaped catalyst body consists of the VPO-containing active composition, including possible auxiliaries such as graphite or pore formers and any further components. On the other hand, it is also possible to apply the active composition to a support, for example an inorganic, oxidic shaped body. Such catalysts are generally referred to as coated catalysts.

As regards the use of the catalyst in the process of the present invention, a number of variants are possible. In the simplest case, all reaction zones of the shell-and-tube reactor unit are charged with the same catalyst bed. In the present context, catalyst bed refers to catalyst material which has the same average composition and the same average activity per volume unit. A catalyst bed can be composed of shaped bodies of the same catalyst, of shaped bodies of a mixture of different catalysts or of shaped bodies (same catalyst or mixture of different catalysts) which are mixed, i.e. "diluted", with an inert material. In a second variant, different catalyst beds are used in different reaction zones. Thus, it may be advantageous to use a less active catalyst bed in the first or one/more of the front end reaction zones and to use a more active catalyst bed in one/more of the downstream reaction zones. Furthermore, it is also possible to use different catalyst beds within one and the same reaction zone. In this variant too, it may be advantageous to use a less active catalyst bed in the vicinity of the reactor inlet and to use a more active catalyst bed further downstream.

Figure 1:
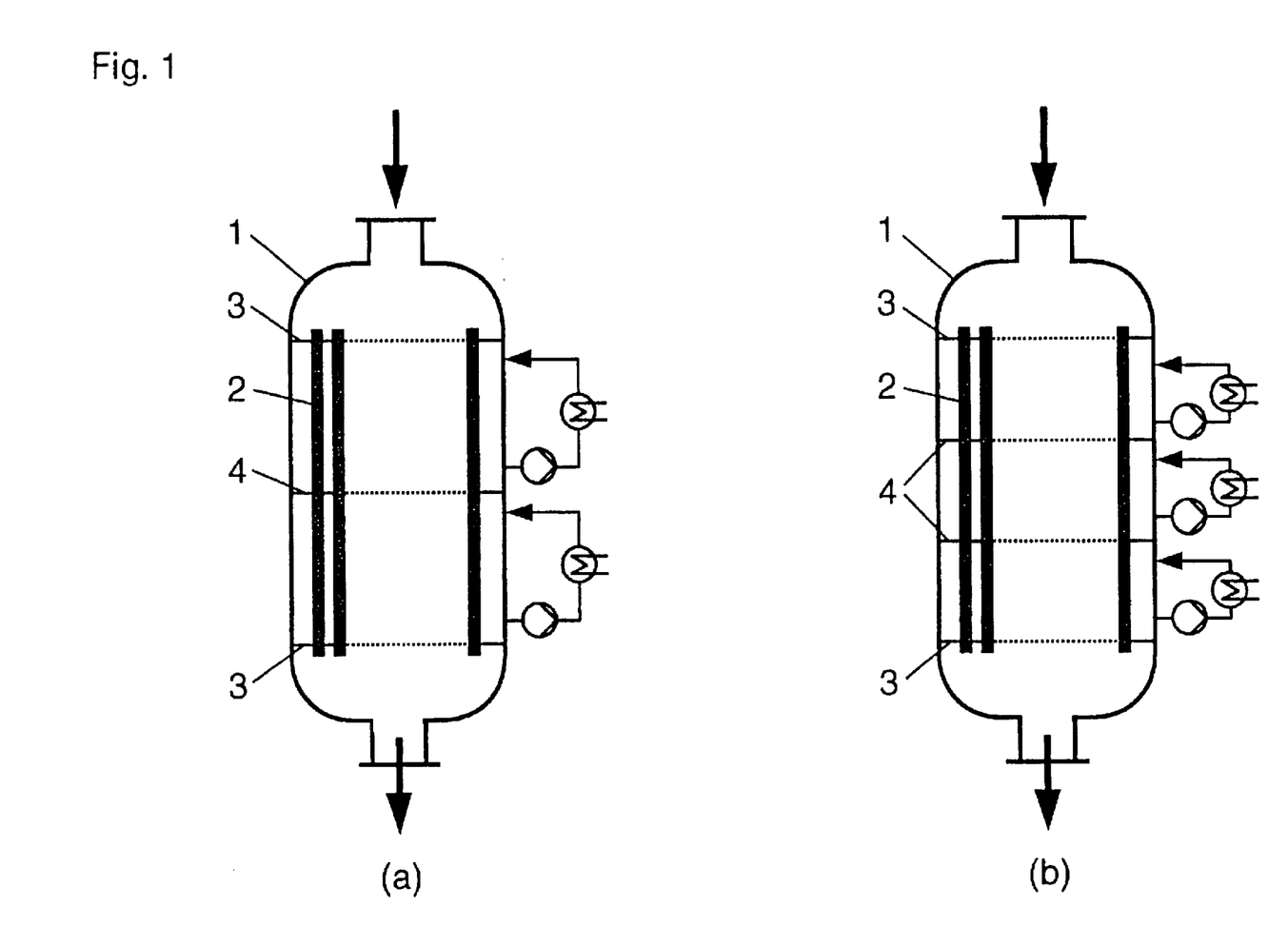

The individual reaction zones can be realized in a single shell-and-tube reactor as multizone shell-and-tube reactor or in a plurality of shell-and-tube reactors connected in series, each of which may again have one or more reaction zones. For the purposes of the present invention, a multizone shell-and-tube reactor is a shell-and-tube reactor which has at least two circuits for heat transfer media and makes it possible to set different temperatures in the individual reaction zones. Industrially, "multizone shell-and-tube reactors" can be realized by, for example, constructing a plurality of thermally insulated circuits for heat transfer media, as shown schematically in FIG. 1. The reactor body (1) contains the individual reactor tubes (2) whose inlet end and outlet end are each welded to a perforated plate (3). Between the two perforated plates, there are then further, thermally insulated perforated-plates (4) which divide the region of the heat transfer medium into a number of separate sections. Each section advantageously has a separate circulation pump or circulation apparatus and a separate heat exchanger.

FIG. 1a schematically shows a two-zone shell-and-tube reactor, while FIG. 1b shows a three-zone shell-and-tube reactor. According to the invention, the heat transfer media can be passed through the space surrounding the reaction tubes in cocurrent to the gas mixture flowing through the reaction tubes, as shown in FIGS. 1a and 1b, or in countercurrent. Of course, the flow directions of the heat transfer media in the individual zones may also be different according to the present invention. As heat transfer media, preference is given to using salt melts. The division into the individual reaction zones can be at equal intervals, but can also deviate significantly therefrom.

The process of the present invention is advantageously carried out using a shell-and-tube reactor unit having two, three or four successive reaction zones. Preference is given to using a two-zone shell-and-tube reactor, a three-zone shell-and-tube reactor or a four-zone shell-and-tube reactor.

Particular preference is given to carrying out the process in two successive reaction zones, in which case the use of a two-zone shell-and-tube reactor is particularly preferred. Suitable industrial embodiments are described, for example, in DE-A 22 01 528, DE-A 25 13 405, DE-A 28 30 765, DE-A 29 03 582, U.S. Pat. No. 3,147,084 and EP-A 0 383 224. At this point, attention may be drawn to the specific two-zone reactor disclosed in DE-A 22 01 528 which provides the opportunity of taking part of the hotter heat transfer medium from the "downstream" reaction zone and introducing it into the colder heat transfer medium of the "front end" reaction zone so as to make partial heating possible if desired.

In all the above cases, a transverse flow can also be superposed on the parallel flow of the heat transfer medium relative to the reaction tubes within the respective reaction zone, so that the individual reaction zones correspond to a shell-and-tube reactor as described in EP-A 0 700 714 or EP-A 0 700 893 and an overall meandering flow (viewed in longitudinal section) of the heat transfer medium through the shell-and-tube reactor is obtained.

The reaction mixture is advantageously preheated to the desired reaction temperature, for example in a preheating zone, before being brought into contact with the catalyst.

In the abovementioned shell-and-tube reactors, the reactor tubes are usually made of ferritic steel and typically have a wall thickness of from 1 to 3 mm. Their internal diameter is generally from 20 to 30 mm. The number of reactor tubes per shell-and-tube reactor is usually in a range from 5000 to 35,000, although a number above 35,000 can also be employed in the case of particularly large plants. The reactor tubes are normally homogeneously distributed within the reactor body.

Suitable heat transfer media are, in particular, fluid heating/cooling media. The use of salt melts such as potassium nitrate, potassium nitrite, sodium nitrate and/or sodium nitrite or low-melting metals such as sodium or alloys of various metals is particularly advantageous.

The inflow temperatures of the heat transfer medium are, according to the present invention, from 350 to 450° C. for the first reaction zone and from 350 to 480° C. for the second and each further reaction zone, with care having to be taken to ensure that the difference between the temperature of the hottest reaction zone and the temperature of the coldest reaction zone located upstream of the hottest reaction zone is at least 2° C. according to the present invention.

The process of the present invention can be carried out in two preferred process variants, namely the variant with a "single pass" and the variant with "recirculation".

a) "single pass"

In the "single pass" variant, the conversion of hydrocarbons per pass through the reactor is from 75 to 95% and maleic anhydride and possibly oxygenated hydrocarbon by-products are removed from the output from the reactor. The reaction gas passed through the reactor, in particular the unreacted hydrocarbons, is/are not recirculated in any direct way in the "single pass" variant. The total conversion of hydrocarbons per pass is preferably from 80 to 90%. The remaining tailgas stream, which comprises inert gases, unreacted hydrocarbons and possibly further components which have not been separated off, is generally discharged from the plant.

The concentration of hydrocarbons at the beginning, i.e. at the reactor inlet, is preferably from 1.0 to 4.0% by volume, particularly preferably from 1.5 to 3.0% by volume. The concentration of oxygen at the beginning is preferably from 5 to 50% by volume, particularly preferably from 15 to 30% by volume. The origin of the oxygen used in the process of the present invention is in principle unimportant, as long as no harmful impurities are present. On the basis of simple technical considerations, air is preferred as oxygen source. In the simplest case, this can be used directly or preferably after cleaning to remove particles. Enrichment with oxygen, for example by liquefaction of the air and subsequent distillation or by pressure swing adsorption, is also possible in principle.

The volume hourly space velocity of hydrocarbons over the catalyst is generally at least 20 standard l/l·h, preferably at least 30 standard l/l·h, particularly preferably at least 35 standard l/l·h.

The maleic anhydride can be separated off by, for example, absorption in a suitable absorption medium. Suitable absorption media are, for example, water or organic solvents. In the case of absorption in water, maleic anhydride is hydrated to form maleic acid. Preference is given to absorption in an organic solvent. Suitable organic solvents are, for example, the high-boiling solvents mentioned in WO 97/43242, for example tricresyl phosphate, dibutyl maleate, high molecular weight wax, aromatic hydrocarbons having a boiling point above 140° C. and di-$C_4$–$C_8$-alkyl phthalates, e.g. dibutyl phthalate. Oxygenated hydrocarbon by-products are generally also absorbed in the solvents mentioned. The absorption can be carried out, for example, at from 60 to 160° C. and a pressure of from 0.1 to 0.5 MPa abs or above. Suitable methods of carrying out the absorption are, for instance, passing the gaseous, cooled or uncooled output from the reactor through a vessel filled with absorption liquid or spraying the absorption liquid in the gas stream. Appropriate methods of scrubbing gas streams are known to those skilled in the art.

b) "recirculation"

In the "recirculation" variant, the conversion of hydrocarbons per pass through the reactor is from 30 to 60%, maleic anhydride and possibly oxygenated hydrocarbon by-products are removed from the output from the reactor and at least part of the remaining stream or at least part of the unreacted hydrocarbons, which may have been separated off, is recirculated to the reaction zones. The total conversion of hydrocarbons per pass is preferably from 40 to 50%.

The concentration of hydrocarbons at the beginning, i.e. at the reactor inlet, is preferably at least 2.0% by volume, particularly preferably at least 2.5% by volume. The concentration of oxygen at the beginning is preferably from 5 to 60% by volume, particularly preferably from 15 to 50% by volume. The origin of the oxygen used in the process of the present invention is in principle unimportant, as long as no harmful impurities are present. From simple technical considerations, the oxygen used generally originates from air, which is usually enriched in oxygen. This enrichment can be carried out, for example, by liquefaction of the air and subsequent distillation or by pressure swing adsorption. Preference is given to using an oxygen-containing gas having an oxygen concentration of from 20 to 100% by volume.

The volume hourly space velocity of hydrocarbons over the catalyst is generally at least 20 standard l/l·h, preferably at least 30 standard l/l·h, particularly preferably at least 35 standard l/l·h.

The integrated total conversion of hydrocarbons, i.e. the conversion based on the total plant, is from 80 to 100%, preferably from 90 to 100%, in the "recirculation" variant of the process of the present invention.

The maleic anhydride can be separated off, for example, as described under (a).

In the process variant with "recirculation", the gas stream remaining after separating off maleic anhydride or at least the unreacted hydrocarbons therein present is/are at least partly recirculated to the reaction zones.

(i) In the case of recirculation of the gas stream without increasing the concentration of the hydrocarbons, it is advantageous to discharge part of the gas stream from the plant (purge stream) to counter accumulation of impurities. The remaining gas stream can generally be recirculated to the reaction zones. The corresponding amount of consumed hydrocarbon and oxygen is added in the customary way.

(ii) To reduce, for example, the amount of inert gas to be recirculated, it may be advantageous to increase the concentration of the hydrocarbons present. Depending on the type of hydrocarbons used, various methods can be considered. Examples of suitable methods are condensation or adsorption on suitable adsorbents (e.g. in the form of a pressure swing adsorption or temperature swing adsorption). Thus, for example, to increase the concentration of n-butane, it is possible to employ adsorption on activated carbon or zeolites with subsequent desorption under reduced pressure and/or at elevated temperature.

The "single pass" and "recirculation" variants described represent two preferred specific cases of the process of the present invention. They in no way restrict the possible use of other variants, nor do they imply a restriction to the process parameters mentioned as preferred.

The independent temperature control of the various reaction zones makes it possible to react in a targeted way to fluctuations in the quantity, quality or purity of the starting materials or to progressive catalyst deactivation and also makes it possible to obtain a stable and high yield of maleic anhydride. Thus, for example, in the case of catalyst deactivation in the first reaction zone (e.g. as a result of catalyst poisons which deactivate the upper layers of the VPO catalyst or due to thermal deactivation in the region of the hot spot maximum of the first reaction zone), the conversion can be restored by increasing the temperature of this first reaction zone. Furthermore, targeted setting of the temperatures of the individual reaction zones makes possible a targeted setting of the conversions in these reaction zones, which exercises an influence on the selectivity and thus on the yield.

The maleic anhydride obtained can, for example, be further processed to give γ-butyrolactone, tetrahydrofuran, 1,4-butanediol or mixtures thereof. Suitable methods are known to those skilled in the art. For the sake of completeness, reference is made to the two documents WO 97/43234 (direct hydrogenation of maleic anhydride in the gas phase) and WO 97/43242 (hydrogenation of a diester of maleic acid in the gas phase).

The invention further provides an apparatus for preparing maleic anhydride by the process of the present invention, by heterogeneously catalyzed gas-phase oxidation of hydrocarbons having at least four carbon atoms using oxygen-containing gases in the presence of a volatile phosphorus compound, comprising a) a quantity-regulated feed unit for the hydrocarbon, for the oxygen-containing gas and possibly for the phosphorus compound, b) a shell-and-tube reactor unit which has at least two successive cooled reaction zones and makes it possible to set different temperatures in the individual reaction zones and c) a unit for separating off the maleic anhydride formed and possibly oxygenated hydrocarbon by-products.

An essential aspect of the apparatus of the present invention is the existence of units (a), (b) and (c) arranged successively in the flow direction. The units specified can follow one another either directly or indirectly via further interposed units or apparatuses. This includes equipment and connections which make it possible to introduce and/or remove mass and/or energy. The three units are described in more detail below.

a) Feed unit

The feed unit ensures quantity-regulated introduction of the hydrocarbon, of the oxygen-containing gas, possibly of the inert gas and possibly of the phosphorus compound. The hydrocarbons can be metered in either in liquid form or in gaseous form. Preference is given to metered addition as a liquid phase.

The oxygen-containing gas and any inert gas are added in gaseous form. Preference is given to adding only one gas which has the desired composition. In the "single pass" variant, this is preferably air, while in the "recirculation" variant it is preferably a gas having an oxygen content higher than that of air.

The volatile phosphorus compound is preferably added separately in liquid form. However, it is also possible to introduce the volatile phosphorus compound in the desired amount into the hydrocarbon upstream of the plant. In this case, the corresponding addition unit is omitted on the apparatus.

The order of addition is of no importance for successful implementation of the process. Thus, all streams can be metered into the plant successively in any order or, for example, together at one point. It is important that the feed be intensively mixed before entering the first reaction zone. Mixing can be carried out, for example, in a static mixer which is located between the feed unit and the shell-and-tube reactor unit. However, the necessary mixing can also be carried out in the shell-and-tube reactor unit by means of appropriate internals. Under these circumstances, the feed unit can also be located directly in the inlet region of the shell-and-tube reactor unit.

If the apparatus is provided with a recirculation facility, this joins the feed gas stream upstream of the mixing unit.

b) Shell-and-tube reactor unit

The shell-and-tube reactor unit is configured as described above. In particular, it has at least two successive reaction zones which make it possible to set different temperatures. The individual reaction zones can be achieved in a single shell-and-tube reactor configured as a multizone shell-and-tube reactor or in a plurality of shell-and-tube reactors connected in series, each of which may again have one or more reaction zones. The shell-and-tube reactor unit preferably comprises a multizone shell-and-tube reactor, particularly preferably a two-zone shell-and-tube reactor, a three-zone shell-and-tube reactor or a four-zone shell-and-tube reactor. Very particular preference is given to using a two-zone shell-and-tube reactor.

c) Unit for separating off the maleic anhydride formed

The maleic anhydride formed is separated off as described above. In particular, it is possible to use various apparatuses suitable for absorption of gases in liquids for this purpose. It is also possible to combine a plurality of identical or different apparatuses for separating off the maleic anhydride to form one unit.

Figure 2:
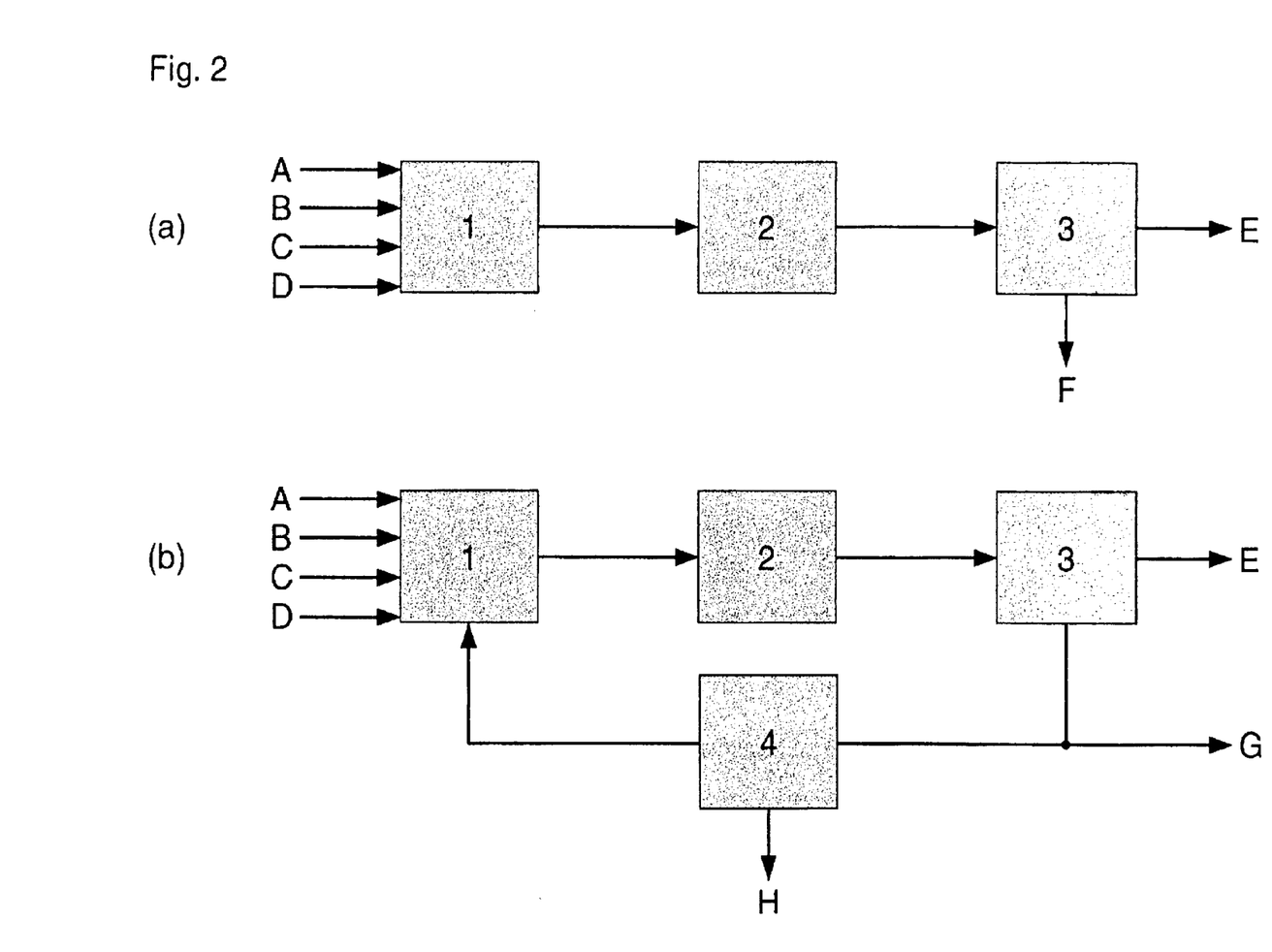

A greatly simplified block diagram of the apparatus of the present invention for the two specific process variants of "single pass" and "recirculation" is shown in FIG. 2.

FIG. 2a shows the "single pass" variant, where (1) is the feed unit, (2) is the shell-and-tube reactor unit and (3) is the unit for separating off the maleic anhydride formed. The streams (A), (B), (C) and (D) correspond to the feed streams hydrocarbon, oxygen-containing gas, if desired inert gas and if desired volatile phosphorus compound. The solution comprising maleic anhydride which is discharged from the plant is designated by stream (E). Stream (F) corresponds to the remaining gas stream which is likewise discharged from the plant.

FIG. 2b shows the "recirculation" variant, where the units (1), (2) and (3) and the streams (A), (B), (C), (D) and (E) have the above meanings. Stream (G) is optional depending on the embodiment and corresponds to the "purge stream" to be discharged from the plant. Likewise optional is the unit (4) which symbolizes the unit for increasing the concentration of the unreacted hydrocarbon and includes a waste gas stream (H). The recirculated hydrocarbon-containing gas is passed to the feed unit (1).

As mentioned above, the units mentioned can be connected in sequence either directly or indirectly by interposition of further units or apparatuses. Examples of further units or apparatuses present therein are, without implying any limitation, heat exchangers (for heating or cooling), pumps (for conveying liquids such as liquid feeds or the solution of the maleic anhydride which has been separated off) or gas compressors (for conveying and compressing gases such as the gaseous feeds or the gas to be recycled in the "recirculation" variant).

In a particularly preferred embodiment for preparing maleic anhydride, n-butane is used as starting hydrocarbon and the heterogeneously catalyzed gas-phase oxidation is carried out in a "single pass" through a shell-and-tube reactor unit having two successive reaction zones. The most significant characteristics of an arrangement preferred for this purpose and of the preferred process are described below.

Air as gas comprising oxygen and inert gas is introduced quantity-regulated into the feed unit. n-butane is likewise fed in at a quantity-regulated rate but preferably in liquid form via a pump and vaporized in the gas stream. The ratio of the amounts of n-butane and oxygen fed in is generally set in accordance with the heat evolved in the reaction and the desired space-time yield and is therefore dependent on, for example, the type and amount of catalyst. As further component, a volatile phosphorus compound, preferably a trialkyl phosphate, is added quantity-regulated to the gas stream. The volatile phosphorus compound can be added, for example, in undiluted form or as a solution in a suitable solvent, for example water. The required amount of the phosphorus compound is dependent on various parameters, for example the type and amount of catalyst or the temperatures and pressures in the plant, and has to be adapted for each system.

The gas stream is intimately mixed by passing it through a static mixer and is heated by passing it through a heat exchanger. The mixed and preheated gas stream is then introduced into the shell-and-tube reactor unit. In the particularly preferred embodiment, this comprises a two-zone shell-and-tube reactor containing a catalyst comprising vanadium, phosphorus and oxygen. The two-zone shell-and-tube reactor can have various engineering configurations. The reader is therefore referred, in particular, to the examples in the description above. Alternatively, the two-zone shell-and-tube reactor can be replaced by two single-zone shell-and-tube reactors of known design connected in series. The relative division of the two reaction zones in terms of catalyst volume depends on various factors, for example the catalyst activity or the desired reaction conditions, and can be adapted to the respective system by a person skilled in the art by means of simple experiments.

The temperature of the shell-and-tube reactor unit is preferably controlled by means of two salt melt circuits. The temperature of the second reaction zone is, according to the present invention, at least 2° C. above that of the first reaction zone. In a particularly preferred embodiment, the two temperatures are set so that, under the given conditions, the temperature of the hot spot maximum of the second reaction zone is above that of the hot spot maximum of the first reaction zone. A conversion of 80–90% is preferably achieved per pass through the reactor.

The product gas stream coming from the shell-and-tube reactor unit is cooled down in a heat exchanger and fed to the unit for separating off the maleic anhydride. In the preferred embodiment, the unit comprises at least one apparatus for the absorptive removal of maleic anhydride and possibly the oxygenated hydrocarbon by-products. Suitable apparatuses are, for example, containers filled with an absorption liquid through which the cooled output gas is passed or apparatuses in which the absorption liquid is sprayed into the gas stream. The solution comprising maleic anhydride is discharged from the plant for further processing or for isolating the desired product. The remaining gas stream is likewise discharged from the plant and, if desired, passed to a unit for recovering the unreacted n-butane.

In a further, particularly preferred embodiment for preparing maleic anhydride using n-butane as starting hydrocarbon, the heterogeneously catalyzed gas-phase oxidation is carried out in a shell-and-tube reactor unit having two successive reaction zones with "recirculation" of at least part of the unreacted n-butane. The feed unit, the shell-and-tube reactor unit and the unit for separating off the maleic anhydride formed are in principle configured as in the preferred "single pass" embodiment described. In the following, only the characteristic differences are therefore described.

Oxygen is preferably used in the form of an enriched gas having an oxygen content of over 20% by volume, for example pure oxygen from fractionation of air. The amounts of the feed components n-butane, oxygen, volatile phosphorus compound and, if used, inert gas are matched to the corresponding operating procedure and the catalyst used. A conversion of 40–50% is preferably achieved per pass through the reactor. Maleic anhydride and possibly the oxygenated hydrocarbon by-products are separated off as described above and discharged from the plant for further processing or for isolation of the desired product. Part of the remaining gas stream, which comprises inert gases and unreacted n-butane, is discharged from the plant in order to counter accumulation of impurities. The major part of the gas is recirculated to the feed unit, mixed with the described starting materials and fed back into the shell-and-tube reactor unit.

The present invention makes it possible to prepare maleic anhydride by heterogeneously catalyzed gas-phase oxidation of a hydrocarbon having at least four carbon atoms by means of oxygen so as to achieve a high hydrocarbon throughput over the catalyst, a high conversion, a high selectivity, a high yield of desired product and a high space-time yield. Space-time yields of 150 g/l·h can be achieved without problems. The present invention also makes possible a long catalyst life at high hydrocarbon throughputs.

A further, important advantage of the invention is the high flexibility of the reaction conditions. The independently adjustable temperatures of the individual reaction zones enable the conversions and selectivities in these reaction zones to be set and optimized in a targeted manner. This makes it possible to specifically counteract a wide variety of influences, for example fluctuations in the quantity, quality or purity of the starting materials or progressive catalyst deactivation.

EXAMPLES

The parameters employed in this text are, unless indicated otherwise, defined as follows:

$$\text{Space-time yield} = \frac{m_{maleic\ anhydride}}{V_{catalyst} \cdot t}$$

$$\text{Space velocity} = \frac{V_{hydrocarbon}}{V_{catalyst} \cdot t}$$

$$\text{Conversion } C = \frac{n^{hydrocarbon}_{reactor,\ in} - n^{hydrocarbon}_{reactor,\ out}}{n^{hydrocarbon}_{reactor,in}}$$

$$\text{Integrated total conversion } c_{tot} = \frac{n^{hydrocarbon}_{plant,\ in} - n^{hydrocarbon}_{plant,\ out}}{n^{hydrocarbon}_{plant,\ in}}$$

$$\text{Selectivity } S = \frac{n_{MA,\ reactor,\ out}}{n_{hydrocarbon,\ reactor,\ in} - n_{hydrocarbon,\ reactor,\ out}}$$

$$\text{Integrated total selectivity } s_{tot} = \frac{n_{MA,plant,out}}{n_{hydrocarbon,\ plant,\ in} - n_{hydrocarbon,\ plant,\ out}}$$

$$\text{Yield } Y = C \cdot S$$

$$\text{Integrated total yield } Y_{tot} = C_{tot} \cdot S_{tot}$$

$$\text{Selectivity } S^{CO+CO2} = \frac{1}{4} \frac{n_{CO+CO2,\ reactor,\ out} - n_{CO+CO2,\ reactor,\ in}}{n_{hydrocarbon,\ reactor,\ in} - n_{hydrocarbon,\ reactor,\ out}}$$

$$\text{Selectivity } S^{CO+CO2}_{tot} = \frac{1}{4} \frac{n_{CO+CO2,\ plant,out} - n_{CO+CO2\ plant,\ in}}{n_{hydrocarbon,\ reactor,\ in} - n_{hydrocarbon,\ reactor,\ out}}$$

$T_p$ temperature of the pth reaction zone
$T_{p,hot\ spot}$ temperature of the hot spot maximum in the pth reaction zone
$m_{maleic\ anhydride}$ mass of maleic anhydride produced [g]
$V_{catalyst}$ catalyst bed volume, summed over all reaction zones [l]
t time [h]
$V_{hydrocarbon}$ volume of hydrocarbon in the gas phase standardized to 0° C. and 0.1013 MPa abs [standard l](Mathematical parameter. If a hydrocarbon is liquid under these conditions, the hypothetical gas volume is calculated via the ideal gas law.)
C conversion of hydrocarbons per pass through the reactor
$C_{tot}$ integrated total conversion of hydrocarbons (i.e. based on the overall plant)
S selectivity to maleic anhydride per pass through the reactor
$S_{tot}$ integrated total selectivity to maleic anhydride (i.e. based on the overall plant)
Y yield of maleic anhydride per pass through the reactor
$Y_{tot}$ integrated total yield of maleic anhydride (i.e. based on the overall plant)
$S_{CO+CO2}$ selectivity to CO plus $C_2$ per pass through the reactor
$S_{tot,CO+CO2}$ integrated total selectivity to CO plus $CO_2$ (i.e. based on the overall plant)
$n_{hydrocarbon,\ reactor,\ in}$ molar flow of hydrocarbons at the reactor inlet [mol/h]
$n_{hydrocarbon,\ reactor,\ out}$ molar flow of hydrocarbons at the reactor outlet [mol/h]
$n_{hydrocarbon,\ plant,\ in}$ molar flow of hydrocarbons at the inlet to the plant [mol/h]
$n_{hydrocarbon,\ plant,\ out}$ molar flow of hydrocarbons at the outlet of the plant [mol/h]
$n_{MA,\ reactor,\ out}$ molar flow of maleic anhydride at the reactor outlet [mol/h]
$n_{MA,\ plant,\ out}$ molar flow of maleic anhydride at the outlet of the plant [mol/h]

Catalyst 1

In a 240 l vessel, 11.8 kg of 100% orthophosphoric acid were dissolved in 150 l of isobutanol with stirring, and 9.09 kg of vanadium pentoxide were subsequently added. This suspension was refluxed for 16 hours and then cooled to room temperature. The precipitate formed was filtered off, washed with isobutanol and dried at 150° C. at 8 kPa abs (80 mbar abs). The dried powder was subsequently treated at 250–300° C. in a rotary tube for 2 hours. After cooling to room temperature, 3% by weight of graphite were added and the powders were intimately mixed. The powder was tabletted to form 5×3×2 mm hollow cylinders. The hollow cylinders were heated in a muffle furnace, initially in air at 7° C./min to 250° C. and subsequently at 2° C./min to 385° C. The catalyst was held at this temperature for 10 minutes, before the atmosphere was switched from air to $N_2/H_2O$ (1:1). The catalyst was heated to 425° C. under the $N_2/H_2O$ atmosphere (1:1) and the system was held at this temperature for 3 hours. Finally, the catalyst was cooled to room temperature under nitrogen.

The catalyst had a bulk density of 0.9 1/kg, a total pore volume of 0.2 ml/g, a BET surface area of 17 $m^2/g$, a phosphorus/vanadium ratio of 1.04–1.05 and a mean oxidation state of the vanadium of +4.1.

Plant 1

The experimental plant was equipped with a feed unit and a reactor tube. Replacement of a shell-and-tube reactor by a reactor tube is very readily possible on a laboratory or pilot plant scale as long as the dimensions of the reactor tube are in the region of those of an industrial reactor tube. The plant was operated in a "single pass".

The hydrocarbon was introduced in liquid form at a quantity-regulated rate via a pump. As oxygen-containing gas, air was introduced at a quantity-regulated rate. Triethyl phosphate (TEP) was likewise added in liquid form, as a solution of 0.25% by weight of TEP in water, at a quantity-regulated rate.

The shell-and-tube reactor unit comprised a two-zone reactor tube. The length of the reactor tube was 6.4 m, the internal diameter was 22.3 mm. A multi-thermocouple with 20 temperature measurement points was located in a protective sheath within the reactor tube. The reactor tube was divided into two reaction zones. Both reaction zones had a length of 3.2 m. They were surrounded by separately heatable/coolable heat transfer medium circuits. Flow through the shell-and-tube reactor was from the top downward. The upper 0.3 m of the reactor tube were filled with inert material and formed the preheating zone. The first and second reaction zones each contained 1.0 l of catalyst 1. As heat transfer medium, use was made of a salt melt. The pressure at the reactor inlet was from 0.1 to 0.4 MPa abs (from 1 to 4 bar abs) in all experiments.

Directly downstream of the shell-and-tube reactor unit, gaseous product was taken off and passed to on-line analysis by gas chromatography. The main stream of the gaseous output from the reactor was discharged from the plant.

All examples were carried out using n-butane as hydrocarbon over catalyst 1 in plant 1.

Since the plant was operated using a "single pass", conversions, selectivities and yields per pass through the reactor are identical to the integrated values for the overall plant.

Example 1

In Example 1A*, the reactor was operated as a single-zone shell-and-tube reactor (not according to the present invention). The temperatures of both reaction zones were 429° C. The gas stream at the beginning, i.e. at the reactor inlet, had an n-butane concentration of 2.0% by volume. The space velocity of n-butane over the catalyst was 40 standard l/l·h. Triethyl phosphate (TEP) was continually fed in as volatile phosphorus compound in an amount of 4 ppm by volume, based on the total amount of gas at the beginning. In the region of the first reaction zone, a hot spot maximum of 455° C. was observed. At a conversion C of n-butane of 85.3%, a yield Y of maleic anhydride of 54.2% was obtained. This corresponds to a space-time yield of 94.9 g/l·h. The experimental data are shown in Table 1.

In Examples 1B to 1G, the n-butane concentration or the space velocity over the catalyst was increased, with both reaction zones now being operated in accordance with the present invention at different temperatures.(two-zone shell-and-tube reactor). In order to counter a yield-reducing rise in the internal reactor temperature at higher space velocities, the temperature of the first reaction zone was decreased compared to Example 1A*. The temperature of the second reaction zone was adapted in accordance with requirements to achieve a high space-time yield. In Example 1G, a space-time yield of 149 g/l·h was achieved at an n-butane concentration of 3.0% by volume and a space velocity over the catalyst of 75 standard l/l·h.

A space-time yield of 149 g/l·h can be achieved without problems by means of the process of the present invention.

Example 2

In Example 2, the reactor was operated as a two-zone shell-and-tube reactor at a constant space velocity of 50 l/l·h, a constant n-butane concentration of 2.0% by volume and a continual introduction of triethyl phosphate (TEP) in an amount of 4 ppm by volume, based on the total amount of gas at the beginning. The conversion C was 85±1% during the trial. The temperatures of the two reaction zones $T_1$ and $T_2$ were varied and thus the difference of the temperatures of the two hot spot maxima $T_{2,hot\ spot} - T_{1,hot\ spot}$ was also varied.

The results are shown in Table 2. In Example 2A according to the present invention, a temperature difference between the two reaction zones $T_2-T_1$ of 2° C. was set. The hot spot maximum of the second reaction zone $T_{2,hot\ spot}$ obtained under these conditions was still relatively weakly pronounced compared to $T_{1,hot\ spot}$ and, at 441° C., was 21° C. lower than $T_{1,hot\ spot}$. Nevertheless, a yield Y of maleic anhydride of 52.4% was obtained.

The temperature difference between the two reaction zones $T_2-T_1$ was increased to values greater than 2° C. by reducing $T_1$ and increasing $T_2$. In Example 2C according to the present invention, $T_2-T_1$ was, for example, 6° C. The altered temperature setting reduced the conversion in the first reaction zone and increased it in the second reaction zone. This is reflected in a lowering of the temperature of the hot spot maximum of the first reaction zone $T_{1,hot\ spot}$ and an increase in the temperature of the hot spot maximum of the second reaction zone $T_{2,hot\ spot}$. The temperature difference $T_{2,hot\ spot} - T_{1,hot\ spot}$ dropped to $-12°$ C., which led to an increase in the yield Y of maleic anhydride to 53.0%.

Lowering $T_1$ further and increasing $T_2$ further enabled a further decrease in the temperature of the hot spot maximum of the first reaction zone $T_{1,hot\ spot}$ and an increase in the temperature of the hot spot maximum of the second reaction zone $T_{2,hot\ spot}$ to be achieved. Thus, values of >0° C. were achieved for the temperature difference $T_{2,hot\ spot} - T_{1,hot\ spot}$. In Example 2E, this was +9° C., i.e. the hot spot maximum of the second reaction zone $T_{2,hot\ spot}$ was 9° C. above the hot spot maximum of the first reaction zone $T_{1,hot\ spot}$. The yield Y of maleic anhydride rose significantly to 54.2%. Compared to Comparative Example 2A*, this corresponds to a yield increase of 3.4% relative.

FIG. 3 shows the dependence of the yield Y of maleic anhydride on the temperature difference between the two hot spot maxima $T_{2,hot\ spot} - T_{1,hot\ spot}$ as determined in Example 2. The yield increases steadily with increasing temperature difference $T_{2,hot\ spot} - T_{1,hot\ spot}$.

With increasing temperature difference between the two hot spot maxima $T_{2,hot\ spot} - T_{1,hot\ spot}$, the yield Y of maleic anhydride increases continually. The highest yields Y are obtained when $T_{2,hot\ spot} - T_{1,hot\ spot} > 0°$ C.

Example 3

Example 3 shows the long-term stability of the VPO catalyst used under the conditions according to the present invention at high space-time yield. Even after over 3300 hours of operation at an n-butane concentration of 3.0% by volume and a space velocity over the catalyst of 75 standard l/l·h, a constant, high space-time yield of 149–150 g/l·h continued to be achieved in the process of the present invention.

The process of the present invention also makes possible stable operation at a high space-time yield of 149–150 g/l·h at high space velocity after over 3300 hours of operation.

Example 4

In Example 4, the reactor was operated as a two-zone shell-and-tube reactor at a high space velocity of 75 standard l/l·h, a constant n-butane concentration of 3.0% by volume and an initial introduction of triethyl phosphate (TEP) in an amount of 4 ppm by volume, based on the total amount of gas at the beginning. The temperatures of the two reaction zones were kept constant at $T_1$=415° C. and $T_2$=422° C.

The results are shown in Table 4. As a further measure of the activity of the catalyst, the selectivity of CO and $CO_2$ formation is reported. At the conditions set, this was in the range from 40.3 to 40.6%. At the time to, the introduction of TEP was stopped and the performance data were determined at intervals of about one hour. After only one hour after the introduction of TEP had been stopped, a decrease in the maleic anhydride selectivity was observed. After about 11 hours, the maleic anhydride selectivity had dropped from the original 57.7% to 54.3%. The selectivity of CO and $CO_2$ formation rose significantly from 40.3 to 44.3%. About 12 hours after stopping the introduction of TEP, the temperature of the hot spot maximum of the first reaction zone had risen from an originally stable 462° C. to over 490° C. A controlled reaction at high selectivity and yield was no longer possible.

Example 4 shows that particularly at high-load operation with a high space velocity over the catalyst, the addition of a volatile phosphorus compound is essential to achieve stable reaction conditions. Without introduction of the phosphorus component or when insufficient phosphorus component is introduced, the activity of the VPO catalyst rises, leading to a significant rise in the temperature of the hot spot maximum of the first reaction zone $T_{1,hot\ spot}$, a significant rise in the conversion C and a decrease in the selectivity S. A runaway reaction is also possible under these circumstances.

Examples 1 to 4 show that the process of the present invention makes it possible to achieve a high conversion, a high selectivity and a high yield of desired product and therefore a high space-time yield at a high space velocity of hydrocarbon over the catalyst. Thus, a space-time yield of 150 g/l·h can be achieved without problems in the gas-phase oxidation of n-butane over VPO catalysts in accordance with the present invention. This high value is reliably maintained even after several thousand operating hours as a result of the stable reaction conditions. Targeted setting of the catalyst activities, the amounts of catalyst and the temperatures of the individual reaction zones make it possible to optimize the yield of maleic anhydride. Thus, the yield rises continually with increasing temperature difference between the hot spot maximum of the second or subsequent reaction zone and a hot spot maximum of an upstream reaction zone. Furthermore, the process of the present invention provides a flexible reaction procedure in respect of the desired high space-time yield, which offers the possibility of optimization even in the case of fluctuations in the quantity, quality or purity of the starting materials or progressive catalyst deactivation.

TABLE 1

Results of Example 1.

| No. | n-Butane conc. [% by volume] | Space velocity [standard l/l · h] | $T_1$ [° C.] | $T_2$ [° C.] | $T_{1,\text{hot spot}}$ [° C.] | $T_{2,\text{hot spot}}$ [° C.] | Conversion C [%] | Selectivity S [%] | Yield Y [%] | Space-time yield [g/l · h] |
|---|---|---|---|---|---|---|---|---|---|---|
| A* | 2.0 | 40 | 429 | 429 | 455 | — | 85.3 | 63.5 | 54.2 | 94.9 |
| B | 2.0 | 40 | 424 | 429 | 449 | 443 | 83.5 | 65.1 | 54.4 | 95.2 |
| C | 2.5 | 50 | 421 | 439 | 457 | 464 | 83.6 | 63.5 | 53.1 | 116 |
| D | 2.0 | 50 | 421 | 433 | 448 | 457 | 85.6 | 63.3 | 54.2 | 119 |
| E | 2.5 | 62.5 | 417 | 425 | 450 | 458 | 80.7 | 61.2 | 49.4 | 135 |
| F | 2.7 | 67.5 | 413 | 425 | 459 | 465 | 80.5 | 57.5 | 46.3 | 137 |
| G | 3.0 | 75 | 412 | 424 | 464 | 466 | 77.3 | 59.0 | 45.6 | 149 |

*Comparative Example

During the entire trial, the following parameters were kept constant: Concentration of triethyl phosphate (TEP) = 4 ppm by volume.

TABLE 2

Results of Example 2.

| No. | $T_1$ [° C.] | $T_2$ [° C.] | $T_2 - T_1$ [° C.] | $T_{1,\text{hot spot}}$ [° C.] | $T_{2,\text{hot spot}}$ [° C.] | $T_{2,\text{hot spot}} - T_{1,\text{hot spot}}$ [° C.] | Yield Y [%] | Space-time yield [g/l · h] |
|---|---|---|---|---|---|---|---|---|
| A | 424 | 426 | 2 | 462 | 441 | −21 | 52.4 | 115 |
| B | 424 | 430 | 6 | 460 | 447 | −13 | 52.9 | 116 |
| C | 422 | 428 | 6 | 457 | 445 | −12 | 53.0 | 116 |
| D | 422 | 432 | 10 | 450 | 454 | 4 | 53.3 | 117 |
| E | 421 | 433 | 12 | 448 | 457 | 9 | 54.2 | 119 |
| F | 419 | 435 | 16 | 445 | 462 | 17 | 53.8 | 118 |

During the entire trial, the following parameters were kept constant:
Conversion C = 85 ± 1%
Concentration of triethyl phosphate (TEP) = 4 ppm by volume
Concentration of n-butane = 2.0% by volume
Space velocity = 50 standard l/l · h.

TABLE 3

Results of Example 3.

| Hours of operation [h] | $T_{1,\text{hot spot}}$ [° C.] | $T_{2,\text{hot spot}}$ [° C.] | Conversion C [%] | Selectivity S [%] | Yield Y [%] | Space-time yield [g/l · h] |
|---|---|---|---|---|---|---|
| 3160 | 464 | 466 | 77.3 | 58.0 | 45.6 | 150 |
| 3310 | 464 | 467 | 77.0 | 59.1 | 45.5 | 149 |

During the entire trial, the following parameters were kept constant:
Concentration of triethyl phosphate (TEP) = 4 ppm by volume
Concentration of n-butane = 3.0% by volume
Space velocity = 75 standard l/l · h
$T_1$ = 412–423° C.
$T_2$ = 424–426° C.

TABLE 4

Results of Example 4.

| Hours of operation | TEP conc. [ppm by volume] | $T_{1,\text{hot spot}}$ [°C.] | $T_{2,\text{hot spot}}$ [°C.] | Conversion C [%] | Selectivity S [%] | $CO + CO_2$ selectivity $S_{CO+CO_2}$ [%] | Yield Y [%] | Space-time yield [g/l · h] |
|---|---|---|---|---|---|---|---|---|
| $t_o - 3$ h | 4 | 461 | n.d. | 77.3 | 57.7 | 40.6 | 44.6 | 146 |
| $t_o$ | 4 → 0 | 461 | n.d. | 78.2 | 57.7 | 40.3 | 45.1 | 148 |
| $t_o + 1$ h | 0 | 465 | n.d. | 78.3 | 57.7 | 40.7 | 45.2 | 148 |
| $t_o + 5$ h | 0 | 467 | n.d. | 79.3 | 56.9 | 41.1 | 45.1 | 148 |
| $t_o + 7$ h | 0 | 469 | n.d. | 79.9 | 56.6 | 41.6 | 45.2 | 148 |
| $t_o + 9$ h | 0 | 471 | n.d. | 80.4 | 56.1 | 42.4 | 45.1 | 148 |
| $t_o + 10$ h | 0 | 475 | n.d. | 80.9 | 55.5 | 43.0 | 44.9 | 147 |
| $t_o + 11$ h | 0 | 482 | n.d. | 82.0 | 54.3 | 44.3 | 44.5 | 146 |
| $t_o + 12$ h | 0 | >490 | n.d. | n.d. | n.d. | n.d. | n.d. | n.d. | n.d.: not determined
During the entire trial, the following parameters were kept constant:
Concentration of n-butane = 3.0% by volume
Space velocity = 75 standard l/l · h
$T_1 = 415°$ C.
$T_2 = 422°$ C.

We claim:

1. A process for preparing maleic anhydride by heterogeneously catalyzed gas-phase oxidation of hydrocarbons having at least four carbon atoms using oxygen-containing gases in the presence of a volatile phosphorus compound over a catalyst comprising vanadium, phosphorus and oxygen in a shell-and-tube reactor unit having at least two successive cooled reaction zones, wherein the temperature of the first reaction zone is from 350 to 450° C., the temperature of the second and further reaction zones is from 350 to 480° C., the temperature difference between the hottest reaction zone and the coolest reaction zone located upstream of the hottest reaction zone is at least 2° C., and at least one hot spot maximum of the second or subsequent reaction zone is higher than all hot spot maxima in previous reaction zones.

2. A process as claimed in claim 1, wherein the temperature difference between the hottest reaction zone and the coolest reaction zone is at least 5° C.

3. A process as claimed in claim 1, wherein the hydrocarbon used is n-butane.

4. A process as claimed in claim 1, wherein the volatile phosphorus compound used is tri($C_1$–$C_4$-alkyl) phosphate.

5. A process as claimed in claim 1, wherein the heterogeneously catalyzed gas-phase oxidation is carried out at a pressure of from 0.1 to 1 Mpa abs.

6. A process as claimed in claim 1, wherein the gas-phase oxidation is operated in a single pass, the conversion of hydrocarbons per pass is from 75 to 90% and maleic anhydride and possibly oxygenated hydrocarbon by-products are removed from the reactor output.

7. A process as claimed in claim 1, wherein the gas-phase oxidation is operated with recirculation, the conversion of hydrocarbons per pass is from 30 to 60%, maleic anhydride and possibly oxygenated hydrocarbon by products are removed from the reactor output and at least part of the remaining stream or at least part of the unreacted hydrocarbons, which may have been separated off, is recirculated to the reaction zones.

* * * * *